| (12) | United States Patent<br>Kim et al. | (10) Patent No.: US 11,361,866 B2<br>(45) Date of Patent: Jun. 14, 2022 |
|---|---|---|

(54) METHODS AND APPARATUS FOR INJURY PREDICTION BASED ON MACHINE LEARNING TECHNIQUES

(71) Applicant: StrongArm Technologies, Inc., Brooklyn, NY (US)

(72) Inventors: Michael Kim, Sunnyside, NY (US); Sivasankara Reddy Bommireddy, Secaucus, NJ (US); Michael Patrick Spinelli, Croton, NY (US); Sean Petterson, Patchogue, NY (US)

(73) Assignee: StrongArm Technologies, Inc., Brooklyn, NY (US)

( * ) Notice: Subject to any disclaimer, the term of this patent is extended or adjusted under 35 U.S.C. 154(b) by 0 days.

(21) Appl. No.: 17/395,152

(22) Filed: Aug. 5, 2021

(65) Prior Publication Data

US 2022/0044820 A1 Feb. 10, 2022

Related U.S. Application Data

(60) Provisional application No. 63/061,403, filed on Aug. 5, 2020.

(51) Int. Cl.
| *G16H 50/30* | (2018.01) |
| *G16H 50/20* | (2018.01) |
| *G16H 10/00* | (2018.01) |
| *G06K 9/62* | (2022.01) |
| *G06V 40/20* | (2022.01) |

(52) U.S. Cl.
CPC ............ *G16H 50/30* (2018.01); *G06K 9/6267* (2013.01); *G06V 40/20* (2022.01); *G16H 50/20* (2018.01); *G16H 10/00* (2018.01)

(58) Field of Classification Search
CPC .................................................. G06Q 50/20-26
See application file for complete search history.

(56) References Cited

U.S. PATENT DOCUMENTS

| 2011/0213628 | A1* | 9/2011 | Peak .................... | G06Q 40/08 705/4 |
| 2012/0123806 | A1* | 5/2012 | Schumann, Jr. ....... | G06Q 40/08 705/4 |
| 2020/0368914 | A1* | 11/2020 | Schroder ................ | G06V 40/10 |

* cited by examiner

*Primary Examiner* — Neal Sereboff
(74) *Attorney, Agent, or Firm* — Greenberg Traurig, LLP

(57) ABSTRACT

Systems and methods of the present disclosure enable injury prediction using one or more processors for receiving a time-varying signal of sensor measurements from a sensor device associated with a user. The processor(s) generate time windows of the time-varying signal, including a series of the sensor measurements across a predetermined time period, and generate motion features based at least in part on the series of the sensor measurements of the time windows. The processor(s) utilize an injury risk classification machine learning model to predict an injury risk during each time window based at least in part on the motion features. An injury alert message is generated based at least in part on the injury risk being predicted; and transmitting the injury alert message to at least one user computing device.

14 Claims, 7 Drawing Sheets

METHODS AND APPARATUS FOR INJURY PREDICTION BASED ON MACHINE LEARNING TECHNIQUES

CROSS REFERENCE TO RELATED APPLICATIONS

This application claims priority to U.S. Provisional Application No. 63/061,403, filed Aug. 5, 2020 and entitled "METHODS AND APPARATUS FOR INJURY PREDICTION BASED ON MACHINE LEARNING TECHNIQUES," which is incorporated herein by reference in its entirety.

BACKGROUND OF TECHNOLOGY

Injury prediction is a non-linear complex task as there are multiple factors measurable and not measurable that can cause an injury.

SUMMARY OF DESCRIBED SUBJECT MATTER

Some embodiments are directed to an apparatus. The apparatus includes a processor; a set of sensors; and a non-transitory memory storing instructions which, when executed by the processor, causes the processor to capture raw sensor data while a user performs a series of activities wearing the set of sensors for a predetermined time. The apparatus converts the raw sensor data into a set of feature values. The apparatus inputs the set of feature values into a trained machine learning model. Thereafter, the trained machine learning model identifies a percentage of the predetermined time correlated with a likelihood that the user will suffer an injury, and transmit to the user at least one action insight message comprising a recommendation to decrease the likelihood that the user will suffer the injury.

BRIEF DESCRIPTION OF THE DRAWINGS

Various embodiments of the present disclosure can be further explained with reference to the attached drawings, wherein like structures are referred to by like numerals throughout the several views. The drawings shown are not necessarily to scale, with emphasis instead generally being placed upon illustrating the principles of the present disclosure. Therefore, specific structural and functional details disclosed herein are not to be interpreted as limiting, but merely as a representative basis for teaching one skilled in the art one or more illustrative embodiments.

DETAILED DESCRIPTION

Various detailed embodiments of the present disclosure, taken in conjunction with the accompanying figures, are disclosed herein; however, it is to be understood that the disclosed embodiments are merely illustrative. In addition, each of the examples given about the various embodiments of the present disclosure is intended to be illustrative, and not restrictive.

FIGS. 1 through 7 illustrate computer based systems and methods for injury predictions based on machine learning techniques.

A technical problem with the prediction of injuries is that there is a lack of devices that can collect data from individuals before, during, and after the injury. Moreover, injury prediction is a non-linear complex task based on multiple measurable and non-measurable factors that can cause an injury.

As explained in more detail below, the technical solutions described herein include the implementation of a wearable device equipped with multiple sensors that collects motion data from individuals and predicts injuries utilizing machine learning techniques.

Figure 1:
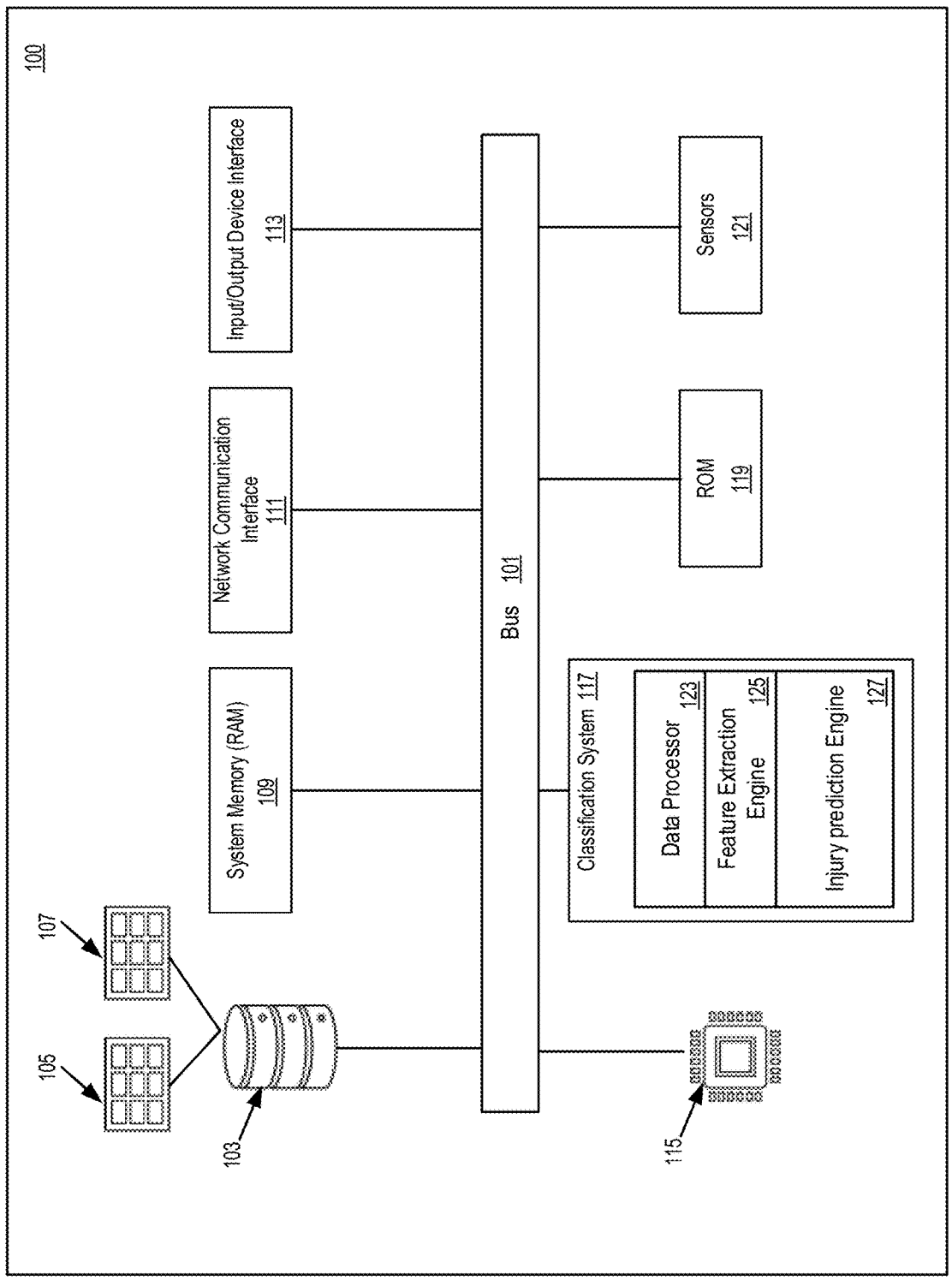
FIGS. 1-7 show one or more schematic flow diagrams, certain computer-based architectures, and/or implementations which are illustrative of some examples of aspects of at least some embodiments of the present disclosure.

FIG. 1 illustrates an example of an implementation of an injury prediction system, in accordance with one or more embodiments of the present disclosure. In some embodiments, the injury prediction system 100 can include a communication bus 101, a processor 115, a classification system 117, a system memory (RAM) 109, a read-only memory (ROM) 119, a record database 103, a set of sensors 121, an input/output device interface such 113, and a network communication interface 111.

In some embodiments, the communication bus 101 collectively represents system, peripheral, and/or chipset buses that communicatively connect the numerous internal devices of the system 100. The communication bus 101 may be a physical interface for interconnecting the various components. In some embodiments, the communication bus 101 may be a network interface, router, switch, or other communication interface.

In some embodiments, the system 100 can include a processor 115 configured to perform instructions provided via the bus 101 by, e.g., instructions retrieved from accessing data stored in memories 109 and 119 via the communication bus 101. In some embodiments, the Read-Only-Memory (ROM) 119 may include a non-volatile storage device, such as, e.g., a magnetic disk hard drive, a solid-state drive, flash memory, or other non-volatile memory and combinations thereof. In some embodiments, system memory 109 may include a volatile memory, such as, e.g., random access memory (RAM) including dynamic RAM and/or static RAM, among other volatile memory devices and combinations thereof. In some embodiments, system memory 109 may store data resulting from processing operations, a cache, or buffer of data to be used for processing operations, operation logs, among other data related to the operation of system 100.

In some embodiments, a record database 103 can store data record sets 105 and 107. In some embodiments, the system 100 may receive, store, or have access to multiple data records stored in the record database 103. Data record sets 105 and 107 can include values captured via sensors 121. Such data records can be associated with movements or motions performed by the same or different users.

In some embodiments, the sensors 121 can include one or more of an accelerometer, a gyroscope, a yaw sensor, a pitch sensor, a roll sensor, a magnetometer sensor, or other suitable sensors. In some embodiments sensors 121 can be strapped to a person or worn in a wearable device (not shown in FIG. 1). In such a case, the sensors 121 can communicate with the system 100 via a wireless or wired communication channel. In some implementations, the wearable device can contain the sensors 121 and other components of the system 100 shown in FIG. 1.

In some embodiments, the classification system 117 can determine user movements and predict user injuries. In some implementations, the classification system 117 can include a data processor 123, a feature extraction engine 125, and an injury prediction engine 127. As further described below, the data processor 123 can compute raw data values captured via the sensors 121 and transform such data values into pre-processed data sets. The feature extraction engine 125 utilize the pre-processed data sets generated by the data processor 123 to generate, for example, multiple time-domain and frequency domain features. The injury prediction engine 127 can implement a machine learning model. Such a machine learning model, can use the features generated by the feature extraction engine 125 to predict when a user will suffer an injury.

In some embodiments the sensors 121 can collect or capture data related to a user's movement at a suitable frequency for characterizing the motion of the user. In some embodiments, the frequency may be selected as any suitable frequency or range of frequencies for data collection, such as any frequency or range of frequencies greater than or equal to 0.05 Hertz (Hz) or greater than or equal to 0.1 Hz. In some embodiments, the frequency or range of frequencies may be as high as 1000 Hz. In some embodiments, the frequency may be selected as, e.g., between within the range of 0.01 to 1000 Hz (inclusive), or may be within 0.1 to 250 Hz (inclusive) or other suitable range, such as, e.g., greater than or equal to 0.05 Hz, greater than or equal to 0.1 Hz, greater than or equal to 1 Hz, greater than or equal to 5 Hz, greater than or equal to 10 Hz, greater than or equal to 12 Hz, greater than or equal to 15 Hz, greater than or equal to 20 Hz, greater than or equal to 25 Hz, greater than or equal to 30 Hz, greater than or equal to 35 Hz, greater than or equal to 40 Hz, greater than or equal to 45 Hz, greater than or equal to 50, between 1 Hz and 1000 Hz, between 1 Hz and 250 Hz, or any other suitable data collection frequency. In some embodiments, a frequency of 12.5 Hz or other suitable frequency is employed to balance movement detail with resource usage. Accordingly, in instances when the sensors 121 capture data at 12.5 Hz, a new raw data set can be generated every 12.5 times per second.

In some embodiments, a user may interact with the system 100 via an input/output interface 113. The input/output interface 113 may include, one or more input peripherals and output peripherals. Input peripherals can include, for example, push buttons, touch screens, switches, keyboards, or other suitable interface that can be utilized by a user to interact with the system 100. The output peripherals can include, for example, touch screens, displays, light emitting diodes, vibrating motors, speakers, or other suitable output peripherals.

As shown in FIG. 1, the communication bus 101 can also couple the system 100 to a network through a network communication interface 111. Accordingly, the system 100 can be part of a network of computers (for example a local area network ("LAN"), a wide area network ("WAN"), or an Intranet, or a network of networks, for example, the Internet and/or cloud environment. Thus, the system 100 can receive inputs and transmit outputs or results to other computing devices via the network communication interface 111.

Figure 2:
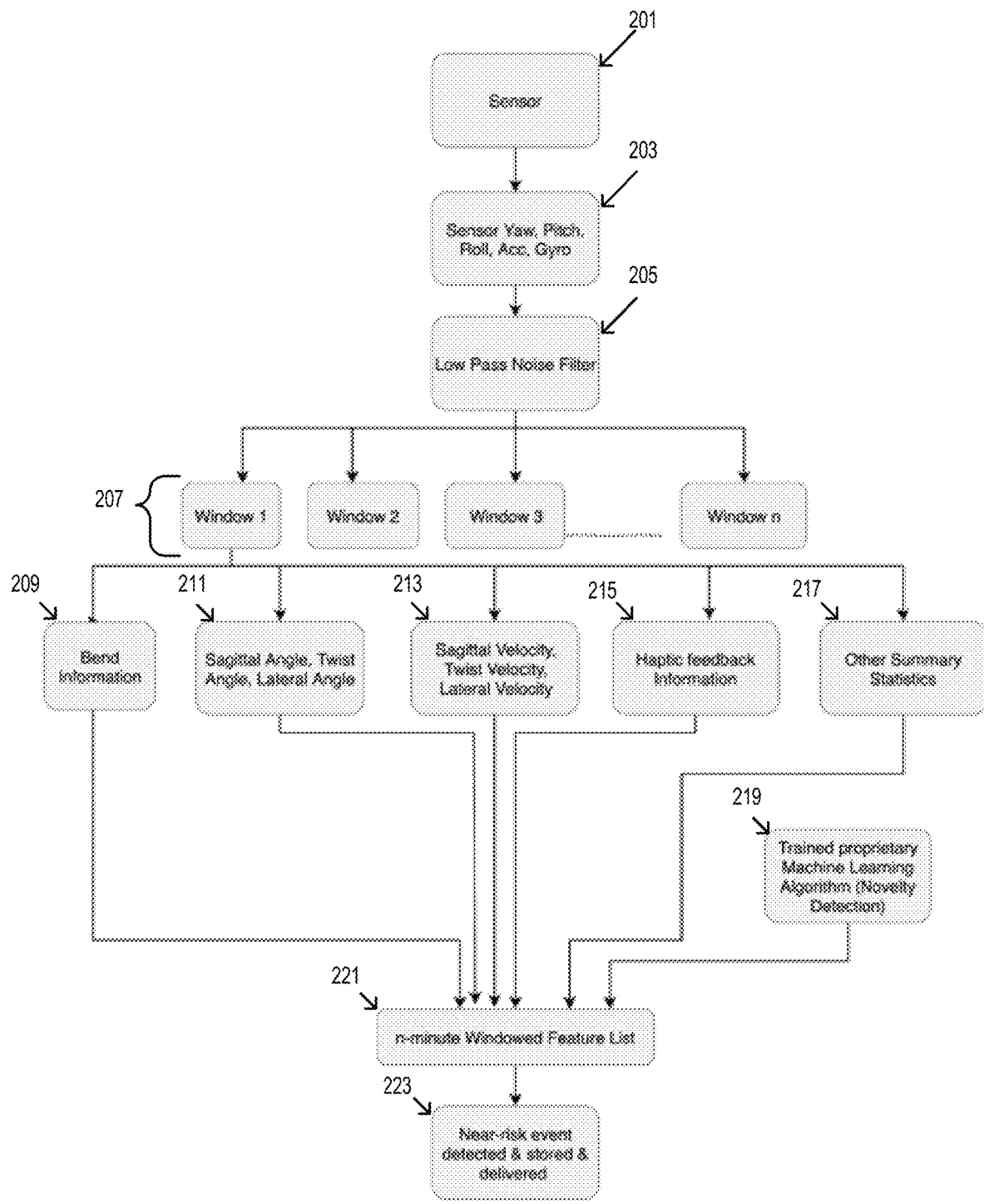

FIG. 2 is a flowchart illustrating examples of computations executed by injury prediction system 100, in accordance with one or more embodiments of the present disclosure. In some instances, sensors 201 can be activated and worn by a person. The sensors 201 can transmit activity data or raw sensor data to the system 100 as shown at 203. Some examples, of such activity data can include captured data associated with users' yaw motions, pitch motions, roll motions, activity data captured via an accelerometer, activity data capture via a gyroscope, activity data acquired via a magnetometer, and other suitable raw sensor data.

In some embodiments, the captured raw sensor data 203 can be processed by the data processor 123, for example, by passing the raw sensor data through a low pass noise filter as shown at 205 or other suitable pre-processing computation. Thereafter, at 207 windows data structures are generated containing values pre-processed by the data processor 123, for examples values filtered by the low pass noise filter 205.

In some embodiments, each raw data set may include data points from each sensor 121, such as, e.g., a timestamp, a yaw measurement, a pitch measurement, a roll measurement, an x-axis acceleration (acc_x) measurement, a y-axis acceleration (acc_y) measurement, a z-axis acceleration (acc_z) measurement, an x-axis gyroscopic (gyro_x) measurement, a y-axis gyroscopic (gyro_y) measurement, a z-axis gyroscopic (gyro_z) measurement, or any other sensor measurement to detect movement or any combination thereof. In some embodiments, each raw data set may be provided as structured or unstructured data, such as, e.g., comma-separated-values (CSV), a data table (e.g., a row and/or column of the data points in a table), a vector, key-value pairs, or any other suitable structured or unstructured data. In some embodiments, for example, the data points may be entered as a row in a table of raw data, where each row is ordered according to the timestamp.

In some embodiments, the data processor 123 can split raw data sets into fixed windows implemented as data structure as the one shown at 207 with an overlap between adjacent windows. In some embodiments, the overlap may be, e.g., a 75% overlap, a 70% overlap, a 65% overlap, a 60% overlap, a 55% overlap, a 50% overlap, a 45% overlap, a 40% overlap, a 35% overlap, a 30% overlap, a 25% overlap, a 20% overlap, a 15% overlap, a 10% overlap between adjacent windows or other suitable overlap. The overlap refers to a ratio of an interval of time spanned by a fixed window and an interval of time spanned by an overlap between adjacent fixed windows.

In some embodiments, the window data structure of 207 may include a window of time that is subdivided into sub-windows, where each sub-window is labelled with the injury prediction engine 127. In some embodiments, by labelling each sub-window, activities and/or tasks may be identified for the window data structure based on the labels for the sub-windows. In some embodiments, rather than labelling the window data structure, the injury prediction engine 127 may label groups of sub-windows based on the labels of the sub-windows in the group.

In some embodiments, the window data structure and each sub-window may be of fixed length. Thus, the number of sub-windows within the window data structure may be based on the length the window data structure and each sub-window and the overlap between adjacent sub-windows. For example, in an instance of sampling data via sensors 121 for 100 seconds at 12.5 Hz, 1250 raw data sets can be captured and if the window 207 is fixed to a value of 10 seconds then there may be 19 windows considering a 5 second overlap between the window; a first window including raw data sets captured during seconds 0-10, a second window including raw data sets captured during seconds 5-15, and so on until a last window including raw data sets captured during seconds 90-100. Each window can have 125 rows of raw data, wherein each row includes a raw data set.

In some embodiments, the feature extraction engine 125 can compute different features on based on the data included in the instantiated window data structures 207. In some embodiments, the features may include time-domain features and/or frequency-domain features for each sub-window of raw data. Example of such features can include, a window start time, a window end time, mean sensor values, standard deviation of sensor values, variance of sensor values, entropy of sensor values, average of maximum and minimum sensor values, number of peaks identified in a Fast Fourier Transform (FFT) signal, number of peaks identified in a Power Spectral Density (PSD) signal, number of peaks identified in an auto-correlation signal, X and Y coordinates of peaks in each of the identified peaks in the FFT signal (e.g., the first five peaks or other suitable number of peaks), the PSD signal, and the auto-correlation signal, cross-correlation measures, zero crossing measures, peak to average ratio, signal magnitude area, signal vector magnitude, differential signal vector magnitude, integration measures, magnitude measures, Hjorth parameters (Mobility, Complexity), and/or other suitable features such as the integral of the accelerometer signal, the integral of the gyroscope signal, the fast Fourier transform of the accelerometer signal, the fast Fourier transform of the gyroscope signal, the power spectral density of the accelerometer signal, the power spectral density of the gyroscope signal, the autocorrelation of the accelerometer signal, the autocorrelation of the gyroscope signal, and other suitable signals.

Examples of such features can include user bending information 209, sagittal angles, twist angles, and/or lateral angles associated with user movements as shown at 211; sagittal velocity, twist velocity, and/or lateral velocity associated with user movements as shown at 213; haptic feedback information associated with user movements as shown at 215; summary statistics 217 associated with user movements (e.g., mean, standard deviation, and variance), and other suitable computations. For example, features calculated from the sensor data may include, e.g., an average twist velocity (avg_twist_velocity), a lift rate (lift rate), a maximum flexion of a joint (max flexion), an average flexion of a joint (average flexion), a maximum lateral movement (max_lateral), an average lateral movement (average_lateral), a maximum lateral movement velocity (max_lateral_velocity), a maximum rotational moment (max_moment), a safety score (safety score), or other data representing movement or any combination thereof.

In some embodiments, the feature extraction engine 125 can receive pre-processed sensor data from the data processor 123. The feature extraction engine 125, can compute or extract multiple features from the pre-processed sensor data, for example, average twist velocity, lift rate, maximum flexion, average flexion, maximum lateral motion, average lateral motion, maximum lateral velocity, maximum moment, safety scores, and other suitable features. Likewise, the feature extraction engine 125 can compute user experience (e.g., days), number of complete motion files associated with the user, number of bad bends performed by the user (e.g., number of bad bends detected in a user's motion file), count of alarms emitted by the system 100 when the user is performing some dangerous or risky movements, maximum and/or minimum values of data captured by the sensors, and other suitable features.

In some embodiments, the features generated at 209, 211, 213, 215, and 217 and other suitable features as discussed above, can be stored in an n-minute windowed feature list 221. The n-minute feature list can include features extracted from sensor data captured during an n-minute window time. In some instances, the trained machine learning model 219 can utilize the values stored in the n-minute windowed feature list 221 to predict near miss events, for example, near-miss injury events. Such near miss events can be stored by the system 100, and/or presented to the user.

In some embodiments, the injury prediction engine (discussed with reference to FIG. 1) can implement the trained machine learning model 219. The trained machine learning model 219 can be, for example, a novelty detection machine learning model. A novelty detection machine learning model can classify data that differ in some respect from the data available during the training phase of the machine learning model. In some instances, novelty detection machine learning models are referred to "one-class classifiers", because such models can be implemented to describe "normal" training data. Novelty detection machine learning models can be used, for example, when the quantity of available "abnormal" data is insufficient to construct explicit models for non-normal classes. Application includes inference in datasets from critical systems, where the quantity of available normal data is very large, such that "normality" may be accurately modelled.

In some embodiments, the machine learning model 219 can be trained with historical or past motion data (e.g., sensor data and/or window data structures) collected from users via the sensors 121. In some embodiments, such data (training data) can include data collected from a user prior to, during, and after such a user suffered an injury. In some implementations, the machine learning model 219 can be trained from data collected via the sensors 121 from, for example, users who have suffered an injury (injured persons) and users who have not suffered an injury (non-injured persons).

In some embodiments, the training data can include historical motion data collected from injured users before such users suffered an injury. Such training data can be labeled as "injured data." Likewise, the training data can include motion data collected from non-injured users. Such training data can be labeled as "non-injured data." Training data labeled as "injured data" and "non-injured data" can be used to implement different binary-prediction machine learning models trained via supervised machine learning techniques.

However, in some embodiments, only training data labeled as "non-injured data" can be used to implement, for example, a novelty detection machine learning model trained via unsupervised machine learning techniques. The novelty detection machine learning model may be configured to identify novel motions and/or actions, where the novel motions and/or actions include any motion and/or action that the novelty detection machine learning model cannot classify as non-injured data. Thus, in some embodiments, the novelty detection machine learning model can be configured as an anomaly detection algorithm that is trained as a one-class classification algorithm to classify data as non-injured data. Thus, the novelty detection machine learning model may be trained on data labelled as non-injured data to detect data that is indicative of a non-injury risk motion data, and any motion data that is not classified as non-injured data may be flagged as a near-risk event.

Some examples of machine learning models that can be used to implement the machine learning model 219 can include density based machine learning models such as a one-class support vector machine learning model or local outlier factor machine learning model, tree-based machine learning models such as an isolation forest model, variance based machine learning models such a robust covariance machine learning model, or other suitable machine learning models.

In some embodiments, the trained machine learning model 219 can received, for example, unseen motion files e.g., n-minute feature list 221 and classify the motion files as "Motion file close to non-injured motion" or "Motion file NOT close to non-injured motion." The motion files classified as "Motion file NOT close to non-injured motion" can be interpreted as "Near miss of Injury." In some implementations, a prediction of a future user injury can be computed as a function of instances classified as a "Near miss of Injury." Accordingly, in some implementations, the system 100 can provide an action insight to the user, for example, recommendations related to how to perform a movement in a safety manner to prevent a future injury.

In some embodiments, a novelty detection machine learning model can be implemented utilizing an elliptical envelope computational technique. An elliptical envelope computational technique can model data as a high dimensional Gaussian distribution with possible covariances between feature dimensions. Such model can identify a boundary ellipse that contains most of the data. Any data outside of the ellipse can be classified as anomalous e.g., a "Motion file NOT close to non-injured motion" or a "Near miss of injury." In some implementations, the Elliptical Envelope routine can use a FAST-Minimum Covariance determinate to estimate the size and shape of the ellipse. In some implementation, the machine learning models discussed above can reach an accuracy of at least 93.8% i.e., the different implementations of machine learning models discussed above can accurately predict when a user is exposed to a "Near miss of injury" at least 93.8% of the time.

In some embodiments, data imbalance, for example imbalance between data labeled as "injured data" and "non-injured data" can be mitigated by the system 100 by the application of multiple computation techniques including, synthetic minority oversampling techniques, up-sampling techniques, under-sampling techniques, weighting techniques, or other suitable techniques to mitigate data imbalance.

In some embodiments, only non-injured training data can be used to train the machine learning model 219. For example, the non-injured training data can be split into a training data set and a testing dataset, the testing dataset can also include injured data to evaluate the capacity of the machine learning model to identify novel or abnormal instances.

Figure 3:
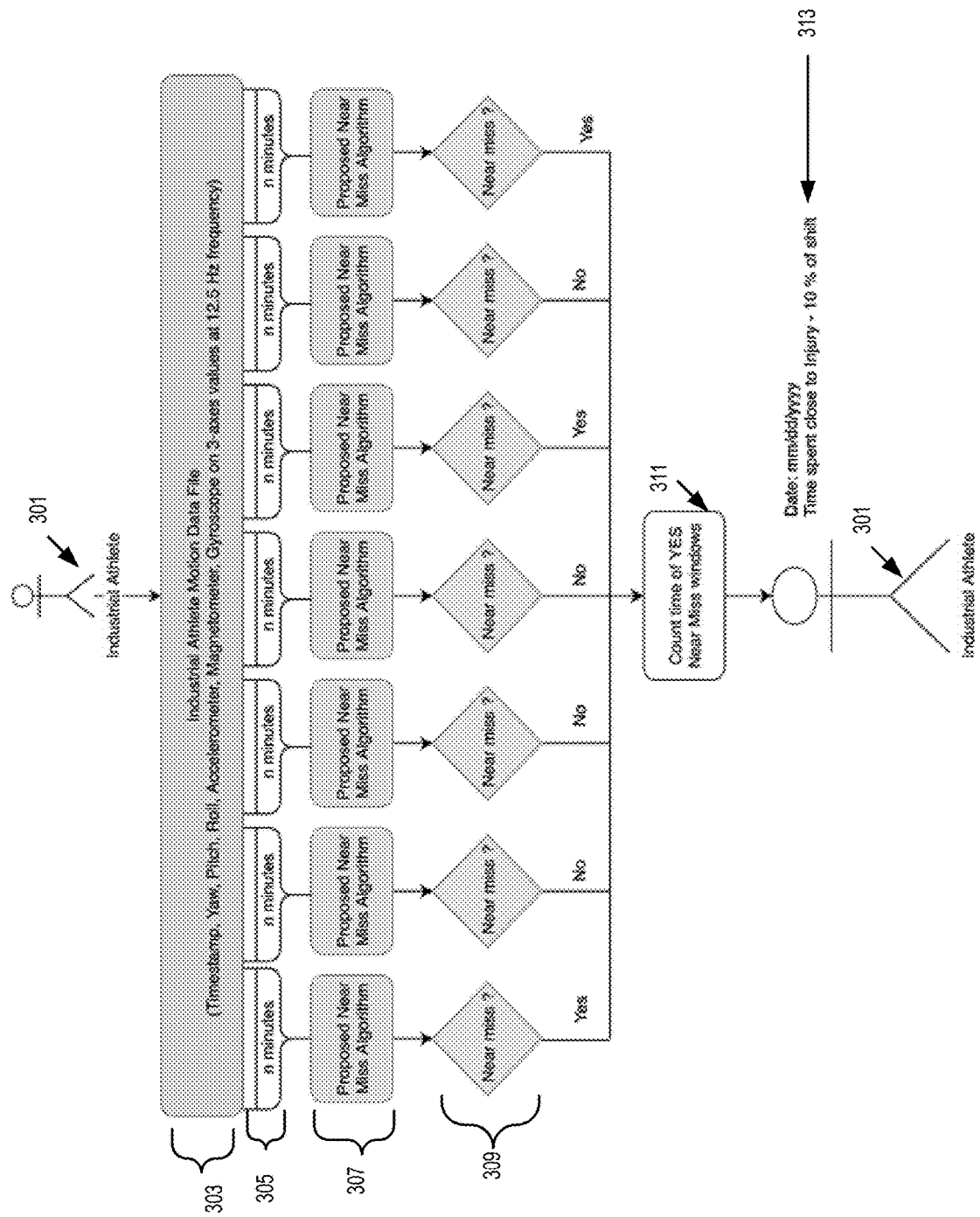

FIG. 3 is a flowchart illustrating examples of computations executed by the injury prediction system 100, in accordance with one or more embodiments of the present disclosure. In some instances, a user 301 (e.g, an industrial athlete) can perform several actions, activities, and/or tasks continuously over time. In some instances, a motion data file 303 can be generated containing sensor data captured by sensors 121 (discussed with reference to FIG. 1) while the user performs actions, activities and/or tasks. The motion data file 303 can include timestamps indicating when a motion is initiated or terminated, and data captured by sensors 121 including yaw sensors, pitch sensors, roll sensors, accelerometer sensors, magnetometer sensors, and gyroscope sensors on 3 axes values. In some implementations, the sensor data can be captured at a frequency of 12.5 Hz, however any suitable sampling rate may be employed, such as, e.g., such as any frequency or range of frequencies greater than or equal to 0.05 Hertz (Hz) or greater than or equal to 0.1 Hz. In some embodiments, the frequency or range of frequencies may be as high as 1000 Hz. In some embodiments, the frequency may be selected as, e.g., between within the range of 0.01 to 1000 Hz (inclusive), or may be within 0.1 to 250 Hz (inclusive) or other suitable range, such as, e.g., greater than or equal to 0.05 Hz, greater than or equal to 0.1 Hz, greater than or equal to 1 Hz, greater or equal to 5 Hz, greater than or equal to 10 Hz, greater than or equal to 12 Hz, greater than or equal to 15 Hz, greater than or equal to 20 Hz, greater than or equal to 25 Hz, greater than or equal to 30 Hz, greater than or equal to 35 Hz, greater than or equal to 40 Hz, greater than or equal to 45 Hz, greater than or equal to 50, between 1 Hz and 1000 Hz, between 1 Hz and 250 Hz, or any other suitable data collection frequency. In some implementations, the user can perform various motions over time represented at 305. Thereafter, the classification system 117 via one or more machine learning models represented at 307 can infer or identify when such motions correspond to, for example, a "Motion NOT close to a non-injured motion," i.e., a "Near Miss."

In some embodiments, the "Near Miss" represented at 309 detected by the one or more machine learning models 307 can be used to predict a user injury as shown at 311. For example, a user injury can be predicted as function of the number of instances classified as "Near Miss" by the one or more machine learning models 307.

In some embodiments, the injury prediction system 100 can transmit an injury alert message 313 to the user 301 via, for example, input/output device interface 113 (discussed with reference to FIG. 1). For instance, an injury alert message can include a date (Month/Day/Year) and a percentage of time the user 301 spent closed to injury as shown at 313.

Figure 4:
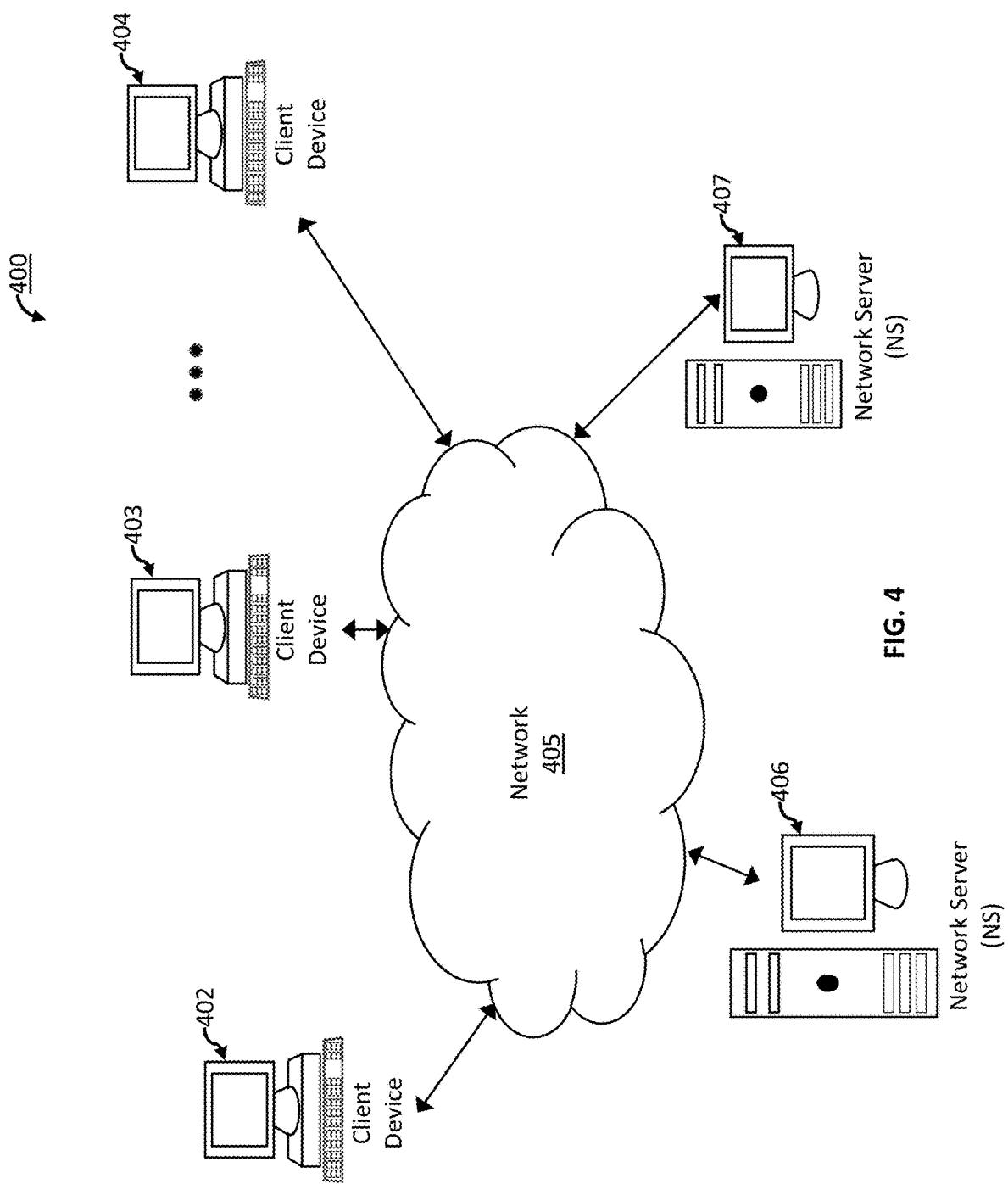

FIG. 4 depicts a block diagram of an exemplary computer-based system and platform 400 in accordance with one or more embodiments of the present disclosure. However, not all of these components may be required to practice one or more embodiments, and variations in the arrangement and type of the components may be made without departing from the spirit or scope of various embodiments of the present disclosure. In some embodiments, the illustrative computing devices and the illustrative computing components of the exemplary computer-based system and platform 400 may be configured to manage a large number of members and concurrent transactions, as detailed herein. In some embodiments, the exemplary computer-based system and platform 400 may be based on a scalable computer and network architecture that incorporates varies strategies for assessing the data, caching, searching, and/or database connection pooling. An example of the scalable architecture is an architecture that is capable of operating multiple servers.

In some embodiments, referring to FIG. 4, member computing device 402, member computing device 403 through member computing device 404 (e.g., clients) of the exemplary computer-based system and platform 400 may include virtually any computing device capable of receiving and sending a message over a network (e.g., cloud network), such as network 405, to and from another computing device, such as servers 406 and 407, each other, and the like. In some embodiments, the member devices 402-404 may be personal computers, multiprocessor systems, microprocessor-based or programmable consumer electronics, network PCs, and the like. In some embodiments, one or more member devices within member devices 402-404 may include computing devices that typically connect using a wireless communications medium such as cell phones, smart phones, pagers, walkie talkies, radio frequency (RF) devices, infrared (IR) devices, CBs citizens band radio, integrated devices combining one or more of the preceding devices, or virtually any mobile computing device, and the like. In some embodiments, one or more member devices within member devices 402-404 may be devices that are capable of connecting using a wired or wireless communication medium such as a PDA, POCKET PC, wearable computer, a laptop, tablet, desktop computer, a netbook, a video game device, a pager, a smart phone, an ultra-mobile personal computer (UMPC), and/or any other device that is equipped to communicate over a wired and/or wireless communication medium (e.g., NFC, RFID, NBIOT, 3G, 4G, 5G, GSM, GPRS, WiFi, WiMax, CDMA, OFDM, OFDMA, LTE, satellite, ZigBee, etc.). In some embodiments, one or more member devices within member devices 402-404 may include may run one or more applications, such as Internet browsers, mobile applications, voice calls, video games, videoconferencing, and email, among others. In some embodiments, one or more member devices within member devices 402-404 may be configured to receive and to send web pages, and the like. In some embodiments, an exemplary specifically programmed browser application of the present disclosure may be configured to receive and display graphics, text, multimedia, and the like, employing virtually any web based language, including, but not limited to Standard Generalized Markup Language (SMGL), such as HyperText Markup Language (HTML), a wireless application protocol (WAP), a Handheld Device Markup Language (HDML), such as Wireless Markup Language (WML), WMLScript, XML, JavaScript, and the like. In some embodiments, a member device within member devices 402-404 may be specifically programmed by either Java, .Net, QT, C, C++, Python, PHP and/or other suitable programming language. In some embodiment of the device software, device control may be distributed between multiple standalone applications. In some embodiments, software components/applications can be updated and redeployed remotely as individual units or as a full software suite. In some embodiments, a member device may periodically report status or send alerts over text or email. In some embodiments, a member device may contain a data recorder which is remotely downloadable by the user using network protocols such as FTP, SSH, or other file transfer mechanisms. In some embodiments, a member device may provide several levels of user interface, for example, advance user, standard user. In some embodiments, one or more member devices within member devices 402-404 may be specifically programmed include or execute an application to perform a variety of possible tasks, such as, without limitation, messaging functionality, browsing, searching, playing, streaming or displaying various forms of content, including locally stored or uploaded messages, images and/or video, and/or games.

In some embodiments, the exemplary network 405 may provide network access, data transport and/or other services to any computing device coupled to it. In some embodiments, the exemplary network 405 may include and implement at least one specialized network architecture that may be based at least in part on one or more standards set by, for example, without limitation, Global System for Mobile communication (GSM) Association, the Internet Engineering Task Force (IETF), and the Worldwide Interoperability for Microwave Access (WiMAX) forum. In some embodiments, the exemplary network 405 may implement one or more of a GSM architecture, a General Packet Radio Service (GPRS) architecture, a Universal Mobile Telecommunications System (UMTS) architecture, and an evolution of UMTS referred to as Long Term Evolution (LTE). In some embodiments, the exemplary network 405 may include and implement, as an alternative or in conjunction with one or more of the above, a WiMAX architecture defined by the WiMAX forum. In some embodiments and, optionally, in combination of any embodiment described above or below, the exemplary network 405 may also include, for instance, at least one of a local area network (LAN), a wide area network (WAN), the Internet, a virtual LAN (VLAN), an enterprise LAN, a layer 3 virtual private network (VPN), an enterprise IP network, or any combination thereof. In some embodiments and, optionally, in combination of any embodiment described above or below, at least one computer network communication over the exemplary network 405 may be transmitted based at least in part on one of more communication modes such as but not limited to: NFC, RFID, Narrow Band Internet of Things (NBIOT), ZigBee, 3G, 4G, 5G, GSM, GPRS, WiFi, WiMax, CDMA, OFDM, OFDMA, LTE, satellite and any combination thereof. In some embodiments, the exemplary network 405 may also include mass storage, such as network attached storage (NAS), a storage area network (SAN), a content delivery network (CDN) or other forms of computer or machine readable media.

In some embodiments, the exemplary server 406 or the exemplary server 407 may be a web server (or a series of servers) running a network operating system, examples of which may include but are not limited to Apache on Linux or Microsoft IIS (Internet Information Services). In some embodiments, the exemplary server 406 or the exemplary server 407 may be used for and/or provide cloud and/or network computing. Although not shown in FIG. 4, in some embodiments, the exemplary server 406 or the exemplary server 407 may have connections to external systems like email, SMS messaging, text messaging, ad content providers, etc. Any of the features of the exemplary server 406 may be also implemented in the exemplary server 407 and vice versa.

In some embodiments, one or more of the exemplary servers 406 and 407 may be specifically programmed to perform, in non-limiting example, as authentication servers, search servers, email servers, social networking services servers, Short Message Service (SMS) servers, Instant Messaging (IM) servers, Multimedia Messaging Service (MMS) servers, exchange servers, photo-sharing services servers, advertisement providing servers, financial/banking-related services servers, travel services servers, or any similarly suitable service-base servers for users of the member computing devices 401-404.

In some embodiments and, optionally, in combination of any embodiment described above or below, for example, one or more exemplary computing member devices 402-404, the exemplary server 406, and/or the exemplary server 407 may include a specifically programmed software module that may be configured to send, process, and receive information using a scripting language, a remote procedure call, an email, a tweet, Short Message Service (SMS), Multimedia Message Service (MMS), instant messaging (IM), an application programming interface, Simple Object Access Protocol (SOAP) methods, Common Object Request Broker Architecture (CORBA), HTTP (Hypertext Transfer Protocol), REST (Representational State Transfer), SOAP (Simple Object Transfer Protocol), MLLP (Minimum Lower Layer Protocol), or any combination thereof.

Figure 5:
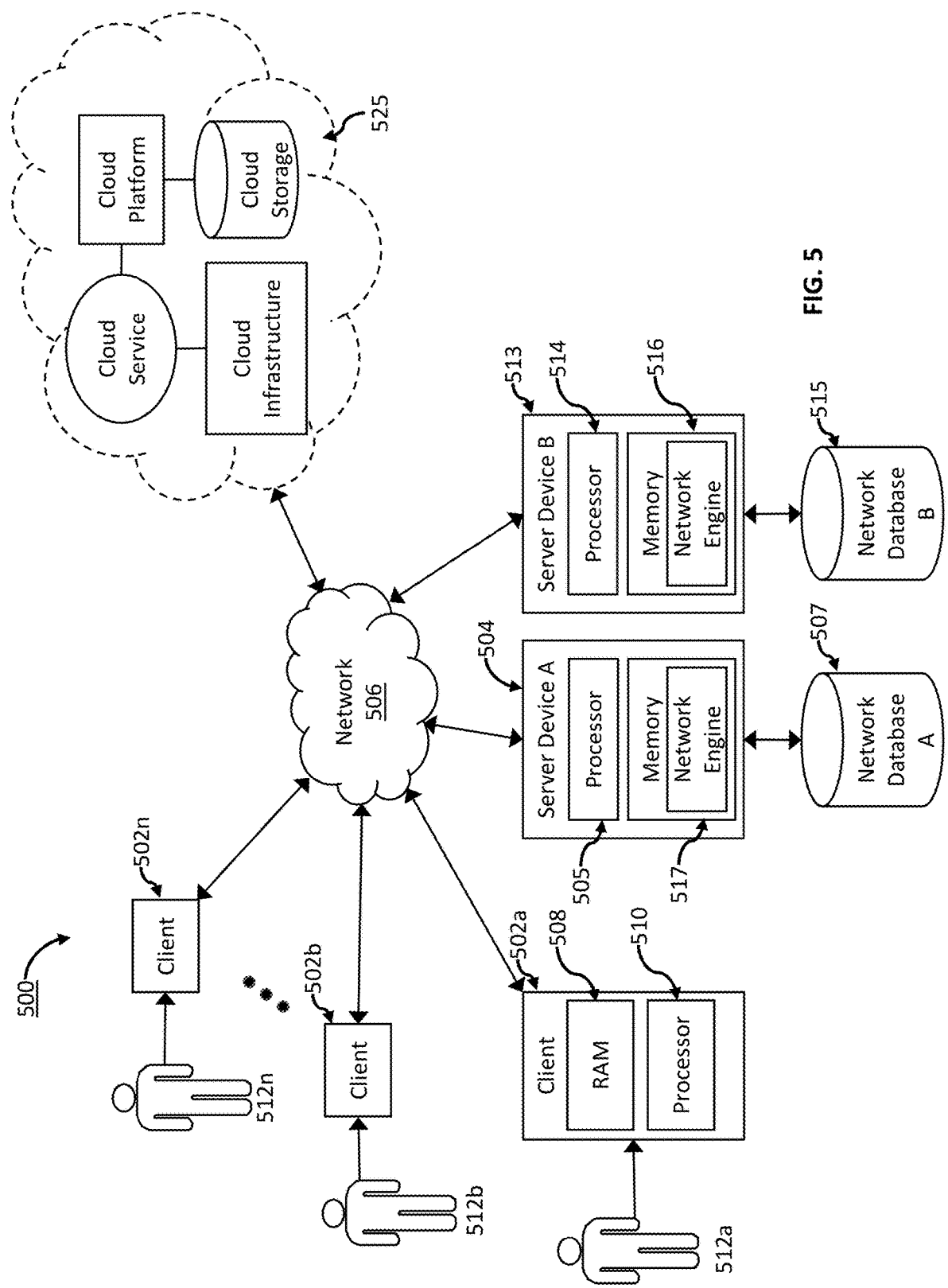

FIG. 5 depicts a block diagram of another exemplary computer-based system and platform 500 in accordance with one or more embodiments of the present disclosure. However, not all of these components may be required to practice one or more embodiments, and variations in the arrangement and type of the components may be made without departing from the spirit or scope of various embodiments of the present disclosure. In some embodiments, the member computing device 502a, member computing device 502b through member computing device 502n shown each at least includes a computer-readable medium, such as a random-access memory (RAM) 508 coupled to a processor 510 or FLASH memory. In some embodiments, the processor 510 may execute computer-executable program instructions stored in memory 508. In some embodiments, the processor 510 may include a microprocessor, an ASIC, and/or a state machine. In some embodiments, the processor 510 may include, or may be in communication with, media, for example computer-readable media, which stores instructions that, when executed by the processor 510, may cause the processor 510 to perform one or more steps described herein. In some embodiments, examples of computer-readable media may include, but are not limited to, an electronic, optical, magnetic, or other storage or transmission device capable of providing a processor, such as the processor 510 of member computing device 502*a*, with computer-readable instructions. In some embodiments, other examples of suitable media may include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. In some embodiments, the instructions may comprise code from any computer-programming language, including, for example, C, C++, Visual Basic, Java, Python, Perl, JavaScript, and etc.

In some embodiments, member computing devices 502*a* through 502*n* may also comprise a number of external or internal devices such as a mouse, a CD-ROM, DVD, a physical or virtual keyboard, a display, or other input or output devices. In some embodiments, examples of member computing devices 502*a* through 502*n* (e.g., clients) may be any type of processor-based platforms that are connected to a network 506 such as, without limitation, personal computers, digital assistants, personal digital assistants, smart phones, pagers, digital tablets, laptop computers, Internet appliances, and other processor-based devices. In some embodiments, member computing devices 502*a* through 502*n* may be specifically programmed with one or more application programs in accordance with one or more principles/methodologies detailed herein. In some embodiments, member computing devices 502*a* through 502*n* may operate on any operating system capable of supporting a browser or browser-enabled application, such as Microsoft™ Windows™, and/or Linux. In some embodiments, member computing devices 502*a* through 502*n* shown may include, for example, personal computers executing a browser application program such as Microsoft Corporation's Internet Explorer™, Apple Computer, Inc.'s Safari™, Mozilla Firefox, and/or Opera. In some embodiments, through the member computing client devices 502*a* through 502*n*, user 512*a*, user 512*b* through user 512*n*, may communicate over the exemplary network 506 with each other and/or with other systems and/or devices coupled to the network 506. As shown in FIG. 5, exemplary server devices 504 and 513 may include processor 505 and processor 514, respectively, as well as memory 517 and memory 516, respectively. In some embodiments, the server devices 504 and 513 may be also coupled to the network 506. In some embodiments, one or more member computing devices 502*a* through 502*n* may be mobile clients.

In some embodiments, at least one database of exemplary databases 507 and 515 may be any type of database, including a database managed by a database management system (DBMS). In some embodiments, an exemplary DBMS-managed database may be specifically programmed as an engine that controls organization, storage, management, and/or retrieval of data in the respective database. In some embodiments, the exemplary DBMS-managed database may be specifically programmed to provide the ability to query, backup and replicate, enforce rules, provide security, compute, perform change and access logging, and/or automate optimization. In some embodiments, the exemplary DBMS-managed database may be chosen from Oracle database, IBM DB2, Adaptive Server Enterprise, FileMaker, Microsoft Access, Microsoft SQL Server, MySQL, PostgreSQL, and a NoSQL implementation. In some embodiments, the exemplary DBMS-managed database may be specifically programmed to define each respective schema of each database in the exemplary DBMS, according to a particular database model of the present disclosure which may include a hierarchical model, network model, relational model, object model, or some other suitable organization that may result in one or more applicable data structures that may include fields, records, files, and/or objects. In some embodiments, the exemplary DBMS-managed database may be specifically programmed to include metadata about the data that is stored.

Figure 6:
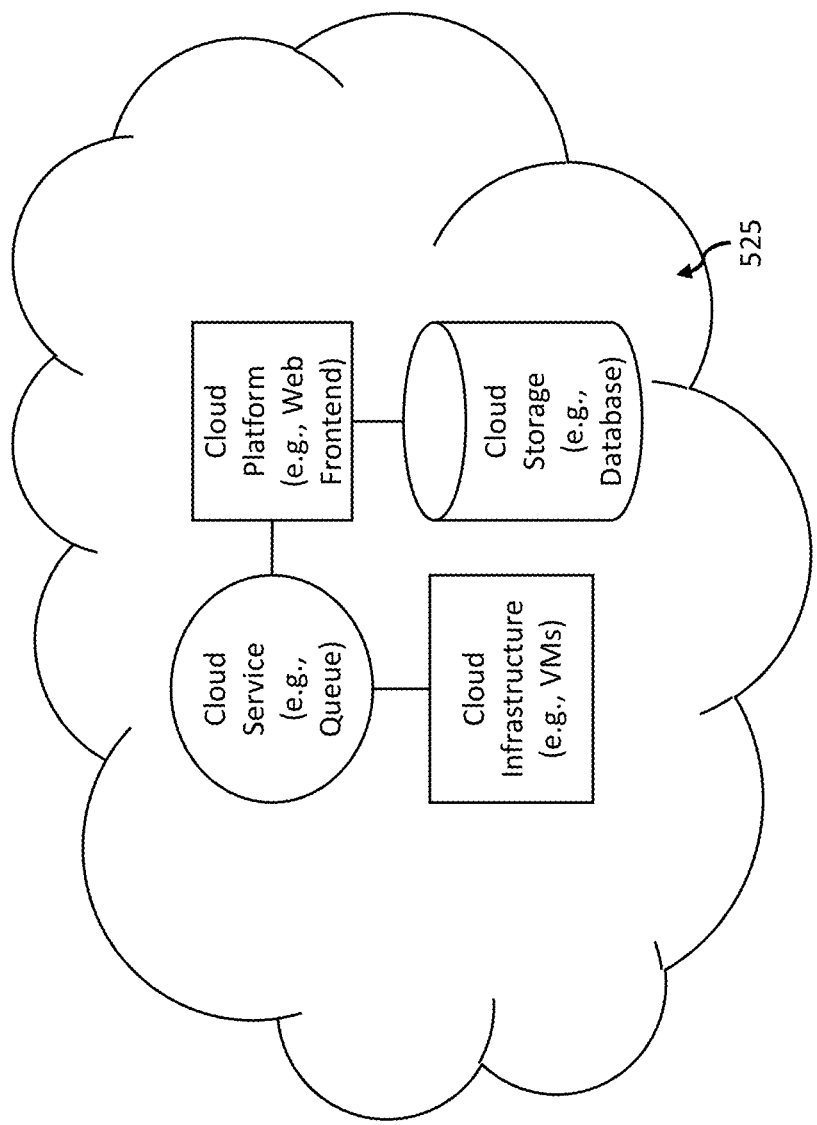
Figure 7:
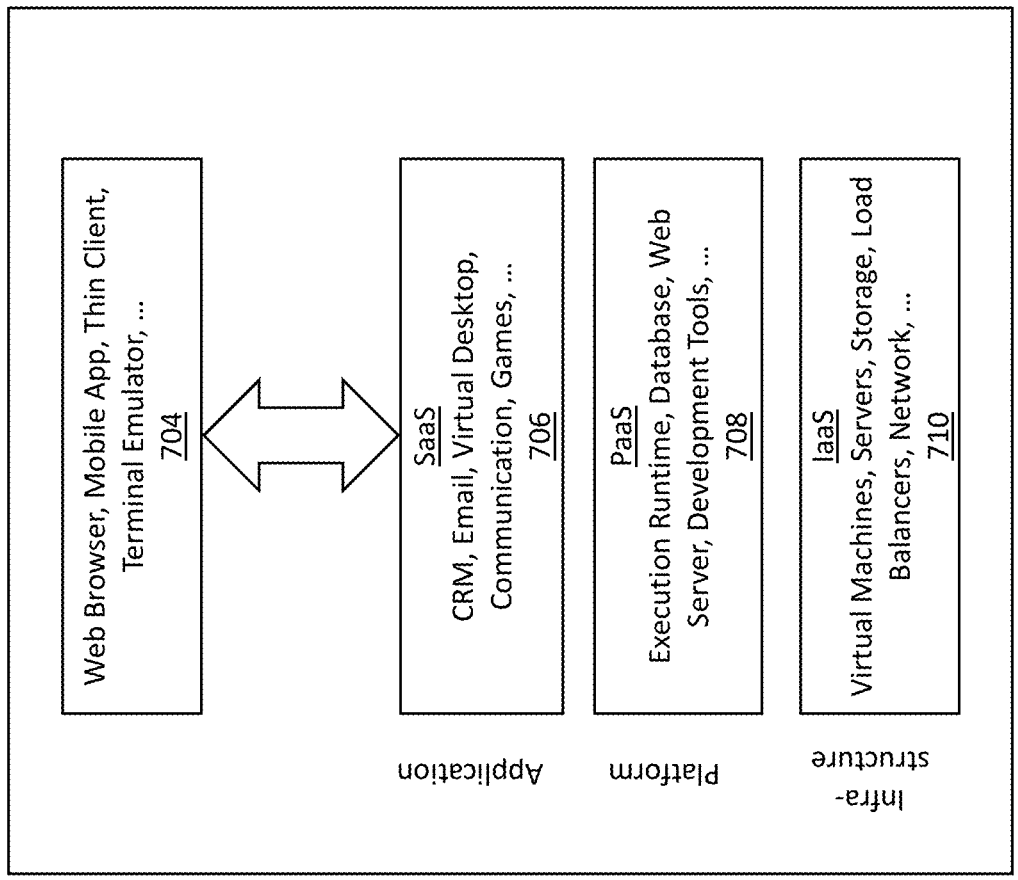

In some embodiments, the exemplary inventive computer-based systems/platforms, the exemplary inventive computer-based devices, and/or the exemplary inventive computer-based components of the present disclosure may be specifically configured to operate in a cloud computing/architecture 525 such as, but not limiting to: infrastructure a service (IaaS) 710, platform as a service (PaaS) 708, and/or software as a service (SaaS) 706 using a web browser, mobile app, thin client, terminal emulator or other endpoint 704. FIGS. 6 and 7 illustrate schematics of exemplary implementations of the cloud computing/architecture(s) in which the exemplary inventive computer-based systems/platforms, the exemplary inventive computer-based devices, and/or the exemplary inventive computer-based components of the present disclosure may be specifically configured to operate.

Throughout the specification, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments may be readily combined, without departing from the scope or spirit of the present disclosure.

In addition, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

In some embodiments, programmed computing systems with associated devices can be configured to operate in the distributed network environment, communicating with one another over one or more suitable data communication networks (e.g., the Internet) and utilizing one or more suitable data communication protocols.

In some embodiments, the material disclosed herein may be implemented in hardware and software or firmware or a combination of them or as instructions stored on a non-transitory machine-readable medium, which may be read and executed by one or more processors. A machine-readable medium may include any medium and/or mechanism for storing or transmitting information in a form readable by a machine (e.g., a computing device). For example, a machine-readable medium may include read only memory (ROM); random access memory (RAM); magnetic disk storage media; optical storage media; flash memory devices, and others. In some embodiments, the non-transitory machine-readable medium can include one or more storage devices, and memory devices described above.

Examples of hardware elements may include processors, microprocessors, circuits, circuit elements (e.g., transistors, resistors, capacitors, inductors, and so forth), integrated circuits, Application Specific Integrated Circuits (ASIC), Programmable Logic Devices (PLD), Digital Signal Processors (DSP), Field Programmable Gate Array (FPGA), logic gates, registers, semiconductor device, chips, microchips, chip sets, and so forth. In some embodiments, the one or more processors may be implemented as a Complex Instruction Set Computer (CISC) or Reduced Instruction Set Computer (RISC) processors; x86 instruction set compatible processors, multi-core, or any other microprocessor or Central Processing Unit (CPU). In various implementations, the one or more processors may be dual-core processor(s), dual-core mobile processor(s), and so forth.

Computer systems, and systems, as used herein, can include any combination of hardware and software. Examples of software may include software components, programs, applications, operating system software, firmware, software modules, routines, subroutines, functions, methods, procedures, software interfaces, Application Programming Interfaces (API), computer code, data, data variables, or any combination thereof that can be processed by a computing device as computer-executable instructions.

In some embodiments, one or more of computer-based systems of the present disclosure may include or be incorporated, partially or entirely into at least one Personal Computer (PC), laptop computer, tablet, portable computer, smart device (e.g., smart phone, smart tablet or smart television), Mobile Internet Device (MID), messaging device, data communication device, server computer, and so forth.

In some embodiments, computer-based systems of the present disclosure may be configured to utilize hardwired circuitry and/or hardware components that may be used in place of or in combination with software instructions to implement system 100 consistent with principles of the disclosure. Thus, implementations consistent with principles of the disclosure are not limited to any specific combination of hardware circuitry or hardware components and/or software.

In some embodiments, software specifically programmed in accordance with one or more principles of the present disclosure may also be available as a client-server software application, or as a web-enabled software application. For example, software specifically programmed in accordance with one or more principles of the present disclosure may also be embodied as a software package installed on a hardware device.

In some embodiments, computer-based systems of the present disclosure may be configured to handle numerous concurrent users that may be, but is not limited to, at least 100 (e.g., but not limited to, 100-999), at least 1,000 (e.g., but not limited to, 1,000-9,999), at least 10,000 (e.g., but not limited to, 10,000-99,999), at least 100,000. As used herein, the term "user" shall have a meaning of at least one user.

The aforementioned examples are, of course, illustrative and not restrictive.

At least some aspects of the present disclosure will now be described with reference to the following numbered clauses.

1. An apparatus, comprising:
a processor;
a set of sensors; and
a non-transitory memory storing instructions which, when executed by the processor, causes the processor to:
 capture raw sensor data while a user performs a series of activities wearing the set of sensors for a predetermined time;
 convert the raw sensor data into a set of feature values;
 input the set of feature values into a trained machine learning model;
 output by the trained machine learning model a percentage of the predetermined time correlated with a likelihood that the user will suffer an injury; and
 transmit to the user at least one action insight message comprising a recommendation to decrease the likelihood that the user will suffer the injury.

Publications cited throughout this document are hereby incorporated by reference in their entirety. While one or more embodiments of the present disclosure have been described, it is understood that these embodiments are illustrative only, and not restrictive, and that many modifications may become apparent to those of ordinary skill in the art, including that various embodiments of the methodologies, the systems, and the devices described herein can be utilized in any combination with each other. Further still, the various steps may be carried out in any desired order (and any desired steps may be added and/or any desired steps may be eliminated).

What is claimed is:
1. A method comprising:
receiving, by the at least one processor, at least one historical time-varying signal having at least one historical motion feature for at least one historical time window;
receiving, by the at least one processor, at least one non-injury event label associated with the at least one historical motion features; and
training, by the at least one processor, an injury risk machine learning model with the at least one historical motion features and the at least one non-injury event label;
 wherein the injury risk machine learning model comprises at least one novelty detection algorithm that detects anomalous motion features in the at least one historical time-varying signal based on the training with the at least one historical motion features and the at least one non-injury event label;
receiving, by at least one processor, a time-varying signal of sensor measurements from at least one sensor device associated with at least one user;
generating, by the at least one processor, at least one time window of the time-varying signal, wherein the at least one time window comprises a series of the sensor measurements across a predetermined time period;
generating, by the at least one processor, at least one motion feature based at least in part on the series of the sensor measurements of the at least one time window;
utilizing, by the at least one processor, the injury risk machine learning model to predict an injury risk during the at least one time window based at least in part on the at least one novelty detection algorithm and the at least one motion feature;

generating, by the at least one processor, an injury alert message based at least in part on the injury risk being predicted; and transmitting, by the at least one processor, the injury alert message to at least one user computing device.

2. The method as recited in claim 1, wherein the at least one sensor device comprises at least one accelerometer configured to detect the sensor measurements comprising yaw, pitch, roll, acceleration and gyroscopic measurements.

3. The method as recited in claim 1, further comprising:
determining, by the at least one processor, the injury risk based at least in part on the novelty detection algorithm not predicting the non-injury event in the at least one time window.

4. The method as recited in claim 1, further comprising:
receiving, by the at least one processor, at least one first historical motion feature for at least one historical time window;
receiving, by the at least one processor, at least one non-injury event label associated with the at least one first historical motion features;
receiving, by the at least one processor, at least one second historical motion feature for at least one historical time window;
receiving, by the at least one processor, at least one injury event label associated with the at least one second historical motion features; and
training, by the at least one processor, the novelty detection algorithm with the at least one first historical motion features, the at least one non-injury event label, the at least one second historical motion features, and the at least one injury event label in order to predict a non-injury event, an injury event, or both in the time-varying signal.

5. The method as recited in claim 1, wherein the injury risk classification machine learning model comprises at least one of:
density based machine learning models,
tree-based machine learning models, and
variance based machine learning models.

6. The method as recited in claim 1, wherein the at least one motion feature comprises at least one of:
sagittal angle,
twist angle,
lateral angle,
sagittal velocity,
twist velocity, and
lateral velocity.

7. A system comprising:
at least one processor; and
a non-transitory memory storing instructions which, when executed by the at least one processor, causes the at least one processor to:
receive at least one historical time-varying signal having at least one historical motion feature for at least one historical time window;
receive at least one non-injury event label associated with the at least one historical motion features; and
train an injury risk machine learning model with the at least one historical motion features and the at least one non-injury event label;
wherein the injury risk machine learning model comprises at least one novelty detection algorithm that detects anomalous motion features in the at least one historical time-varying signal based on the training with the at least one historical motion features and the at least one non-injury event label;
receive a time-varying signal of sensor measurements from at least one sensor device associated with at least one user;
generate at least one time window of the time-varying signal, wherein the at least one time window comprises a series of the sensor measurements across a predetermined time period;
generate at least one motion feature based at least in part on the series of the sensor measurements of the at least one time window;
utilize the injury risk machine learning model to predict an injury risk during the at least one time window based at least in part on the at least one novelty detection algorithm and the at least one motion feature;
generate an injury alert message based at least in part on the injury risk being predicted; and
transmit the injury alert message to at least one user computing device.

8. The system as recited in claim 7, wherein the at least one sensor device comprises at least one accelerometer configured to detect the sensor measurements comprising yaw, pitch, roll, acceleration and gyroscopic measurements.

9. The system as recited in claim 7, wherein the instructions which, when executed by the at least one processor, further cause the at least one processor to:
determine the injury risk based at least in part on the novelty detection algorithm not predicting the non-injury event in the at least one time window.

10. The system as recited in claim 7, wherein the instructions which, when executed by the at least one processor, further cause the at least one processor to:
receive at least one first historical motion feature for at least one historical time window;
receive at least one non-injury event label associated with the at least one first historical motion features;
receive at least one second historical motion feature for at least one historical time window;
receive at least one injury event label associated with the at least one second historical motion features; and
train the novelty detection algorithm with the at least one first historical motion features, the at least one non-injury event label, the at least one second historical motion features, and the at least one injury event label in order to predict a non-injury event, an injury event, or both in the time-varying signal.

11. The system as recited in claim 7, wherein the injury risk classification machine learning model comprises at least one of:
density based machine learning models,
tree-based machine learning models, and
variance based machine learning models.

12. The system as recited in claim 7, wherein the at least one motion feature comprises at least one of:
sagittal angle,
twist angle,
lateral angle,
sagittal velocity,
twist velocity, and
lateral velocity.

13. A non-transitory computer readable medium storing instructions which, when executed by at least one processor, are configured to cause the at least one processor to perform steps comprising:

receiving at least one historical time-varying signal having at least one historical motion feature for at least one historical time window;

receiving at least one non-injury event label associated with the at least one historical motion features; and training an injury risk machine learning model with the at least one historical motion features and the at least one non-injury event label;

wherein the injury risk machine learning model comprises at least one novelty detection algorithm that detects anomalous motion features in the at least one historical time-varying signal based on the training with the at least one historical motion features and the at least one non-injury event label;

receiving a time-varying signal of sensor measurements from at least one sensor device associated with at least one user;

generating at least one time window of the time-varying signal, wherein the at least one time window comprises a series of the sensor measurements across a predetermined time period;

generating at least one motion feature based at least in part on the series of the sensor measurements of the at least one time window;

utilizing the injury risk machine learning model to predict an injury risk during the at least one time window based at least in part on the at least one novelty detection algorithm and the at least one motion feature;

generating an injury alert message based at least in part on the injury risk being predicted; and transmitting the injury alert message to at least one user computing device.

14. The non-transitory computer readable medium as recited in claim 13, further comprising instructions which, when executed by the at least one processor, are further configured to cause the at least one processor to perform steps comprising:

determining the injury risk based at least in part on the novelty detection algorithm not predicting the non-injury event in the at least one time window.

* * * * *